United States Patent
Arumugam

(10) Patent No.: US 9,150,751 B2
(45) Date of Patent: Oct. 6, 2015

(54) ONE POT BIOCATALYTIC PEROXIDE MEDIATED CURE

(71) Applicant: Rohm and Haas Company, Philadelphia, PA (US)

(72) Inventor: Selvanathan Arumugam, Blue Bell, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 14/341,893

(22) Filed: Jul. 28, 2014

(65) Prior Publication Data

US 2015/0038639 A1   Feb. 5, 2015

Related U.S. Application Data

(60) Provisional application No. 61/859,918, filed on Jul. 30, 2013.

(51) Int. Cl.

| | |
|---|---|
| C09D 143/04 | (2006.01) |
| C09D 131/04 | (2006.01) |
| C08F 4/34 | (2006.01) |
| C08F 4/32 | (2006.01) |
| C09D 7/12 | (2006.01) |
| C09D 133/14 | (2006.01) |
| C09D 167/08 | (2006.01) |
| C08K 5/14 | (2006.01) |

(52) U.S. Cl.
CPC ............. *C09D 143/04* (2013.01); *C08F 4/32* (2013.01); *C08F 4/34* (2013.01); *C09D 7/1233* (2013.01); *C09D 131/04* (2013.01); *C09D 133/14* (2013.01); *C09D 167/08* (2013.01); *C08K 5/14* (2013.01)

(58) Field of Classification Search
None
See application file for complete search history.

(56) References Cited

U.S. PATENT DOCUMENTS

| | | | |
|---|---|---|---|
| 6,149,977 A * | 11/2000 | Fischer et al. | ............... 427/338 |
| 6,306,991 B1 | 10/2001 | Fischer et al. | |
| 2004/0132912 A1 | 7/2004 | McElwee | |
| 2006/0205908 A1 | 9/2006 | Laur et al. | |
| 2007/0071695 A1 | 3/2007 | Chopra et al. | |
| 2010/0201745 A1 | 8/2010 | Silverbrook | |
| 2011/0091653 A1* | 4/2011 | Overbeek et al. | ......... 427/372.2 |
| 2011/0237420 A1 | 9/2011 | Grote et al. | |

FOREIGN PATENT DOCUMENTS

| | | | |
|---|---|---|---|
| EP | 0321872 | A2 | 6/1989 |
| EP | 426145 | A1 | 5/1991 |
| EP | 916694 | A1 | 5/1999 |
| EP | 1160298 | A1 | 12/2001 |
| EP | 2589629 | A1 | 5/2013 |
| JP | 1163272 | A | 6/1989 |
| JP | 6287516 | A | 10/1994 |
| WO | 0078988 | A1 | 12/2000 |
| WO | 0128960 | A1 | 4/2001 |
| WO | 02072704 | A2 | 9/2002 |
| WO | 2004067582 | A1 | 8/2004 |
| WO | WO 2004067582 | A1 * | 8/2004 |
| WO | 2006123975 | A1 | 11/2006 |
| WO | 2008081951 | A1 | 7/2008 |
| WO | 2010046309 | A1 | 4/2010 |

* cited by examiner

*Primary Examiner* — Satya Sastri
(74) *Attorney, Agent, or Firm* — Reid S. Willis

(57) ABSTRACT

The present invention relates to a composition comprising a stable aqueous dispersion of crosslinkable polymer particles, a peroxidase enzyme, and a hydrophobic hydroperoxide having a 10-hour half life temperature of at least 100° C. The composition provides a robust one-pot peroxidase mediated cure for latex particles bearing a variety of polymerizable functional groups.

9 Claims, No Drawings

ONE POT BIOCATALYTIC PEROXIDE MEDIATED CURE

BACKGROUND OF THE INVENTION

The present invention relates to a one-pot enzyme curable drier package for a waterborne latex formulation.

The impetus to achieve low/zero VOC for water-borne coatings has necessitated the use of soft copolymers to attain film formation without volatile coalescent, at the expense of lower $T_g$s, which adversely impact hardness. Thus, crosslinking agents are typically used to impart hardness during the curing process. Ambient cure in high-performance coatings rely on reactive functional groups in polymer precursors to build three-dimensional cross-linked networks. Conventional curing reagents include oxidation catalysts (transition metal driers), free radical initiators and, chemical cross-linkers to achieve the desired result. Most traditional approaches require a two-pack system because it is often difficult to decouple the pot life from the curing time. Many of these conventional curing additives are disadvantaged by pre-cross-linking, reliance on two-component architecture, and toxicity as with metal driers such as cobalt naphthenate.

EP2589629 describes the use of oxidizing enzymes such as peroxidases and laccases as environmentally friendly substituents for ambient cure metal driers in alkyd systems. WO 01/28960 A1 describes enzymatic ambient crosslinking of synthetic urushi, which contains oxidizable phenolic groups. Nevertheless, ambient cure via enzymatic oxidation is often slow or ineffective in the absence additional additives, which may adversely impact the cure process.

It would therefore be an advance in the art to find a one-pot method for ambient cure of low VOC waterborne binder formulations.

SUMMARY OF THE INVENTION

The present invention addresses a need by providing, in one aspect, a composition comprising a stable aqueous dispersion of crosslinkable polymer particles, a peroxidase enzyme, and a hydrophobic hydroperoxide having a 10-hour half life temperature of at least 100° C.

In a second aspect, the present invention is a method comprising the steps of 1) contacting together a stable aqueous dispersion of crosslinkable polymer particles, a peroxidase enzyme, a hydrophobic hydroperoxide having a 10-hour half life temperature of at least 100° C., a pigment, and a rheology modifier; and 2) applying the mixture from step 1) to a substrate to form a cured coating.

The present invention addresses a need by enabling a robust one-pot room temperature peroxidase mediated cure for latex particles bearing a variety of polymerizable functional groups.

DETAILED DESCRIPTION OF THE INVENTION

In a first aspect, the present invention is a composition comprising a stable aqueous dispersion of crosslinkable polymer particles, a peroxidase enzyme, and a hydrophobic hydroperoxide having a 10-hour half life temperature of at least 100° C. As used herein, "crosslinkable polymer particles" refer to particles of polymer functionalized with activated methylene groups (for example, diallylic groups arising from an alkyd); acetoacetoxy groups (arising, for example, from monomers such as acetoacetoxy ethyl methacrylate); terminal olefin groups; or polyvinyldimethylsiloxane groups. Thus, the dispersions of crosslinkable polymer particles are alkyd-, acetoacetoxy functionalized acrylic-, vinylsiloxane-, or vinyl acetate-based latexes.

The peroxidase enzyme is a water soluble iron-porphyrin enzyme that catalyzes the oxidation of a variety of organic substrates in the presence of the hydrophobic hydroperoxide.

Examples of peroxidase enzymes include horseradish peroxidase, cytochrome c peroxidase, and Glutathione peroxidase. The concentration of the peroxidase is typically from 0.1 to 1.1 weight percent, based on the weight of the latex (typically from 0.05 to 0.5 weight percent based the weight of the binder).

As used herein, term "hydrophobic hydroperoxide" refers to a hydroperoxide having an EPI-Suite calculated LogP in the range of from 0.5 to 5, more preferably in the range of 0.75 to 4. The hydroperoxide is also thermally stable, with a 10-hour half life of at least 100° C. (see Technical bulletin on peroxides from AkzoNobel, LUPEROX, Guangzhou Flying Dragon Chemical Ltd; Polymer Handbook", Eds. Brandrup, J; and Immergut, E. H.; Grulke, E. A., 4th Edition, John Wiley, New York, 1999, II/2-69). The concentration of the hydrophobic hydroperoxide is preferably from 0.02 to 1 weight percent based on the weight of the latex (typically 0.01 to 0.5 weight percent, based on the weight of the binder).

Organic hydroperoxides react at ambient temperature in the presence of an activator; in contrast, organic peroxides, which are not within the scope of the present invention, either need to thermally activated or are too unstable at room temperature to be useful.

Examples of suitable thermally stable hydroperoxides, their LogPs, and their 10-h half life temperatures are cumene hydroperoxide (LogP=2.16, 10-hour $T_{1/2}$=140° C.), t-amyl hydroperoxide (LogP=1.43, 10-hour $T_{1/2}$=153° C.), t-butyl hydroperoxide (LogP=0.94, 10-hour $T_{1/2}$=163° C.), para-menthane hydroperoxide (LogP=3.63, 10-hour $T_{1/2}$=130° C.), isopropylcumyl hydroperoxide (LogP=3.61, 10-hour $T_{1/2}$=129° C.), and 1,1,3,3-tetramethybutyl hydroperoxide (LogP=2.30, 10-hour $T_{1/2}$=140° C.).

Examples of other suitable hydrophobic hydroperoxides include n-butyl hydroperoxide, p-cymene hydroperoxide, lauryl hydroperoxide, benzyl hydroperoxide, cyclohexyl hydroperoxide, cyclohexene hydroperoxide, bromo-t-butyl hydroperoxide, eicosyl hydroperoxide, 1,1-dichloromethyl-propyl hydroperoxide, isopropyl hydroperoxide, sec-butyl hydroperoxide, α,α-dimethylbenzyl hydroperoxide, chloro-t-butyl hydroperoxide, 1-chloromethyl-1-bromomethylpropyl hydroperoxide, 1-methylcyclohexyl hydroperoxide, cyclohexanol hydroperoxide, α,α-dimethyl-p-nitrobenzyl hydroperoxide, 2-chloro-1-hydroxycyclohexyl hydroperoxide, 2-hydroxyethyl hydroperoxide, and α,α-p-nitrobenzyl hydroperoxide. Cumene hydroperoxide is a preferred hydroperoxide.

Because of its water solubility, the peroxidase enzyme preferentially partitions into the aqueous phase of the latex; the hydrophobic hydroperoxide, on the other hand, preferentially partitions into the latex particles, thus ensuring the stability of the formulation prior to casting of the latex onto a substrate. Once the formulation is applied to the substrate, the water evaporation induces contact between the hydrophobic hydroperoxide and the peroxidase enzyme, thereby initiating curing at ambient temperature.

In a second aspect, the present invention is a method for preparing the composition of the present invention. In a first step, the stable aqueous dispersion of the crosslinkable polymer particles, the peroxidase enzyme, and the hydrophobic hydroperoxide are contracted together to form a composition that is stable to reactive crosslinking. Other materials are advantageously included in this step including one or more pigments and rheology modifiers, as well as one or more additives selected from the group consisting of fillers, biocides, surfactants, coalescents, and dispersants. In a second step, the composition is coated onto a substrate to form a coating that cures relatively quickly. It is believed that the peroxidase diffuses into the hydrophobic polymer particles, thereby decomposing the hydrophobic hydroperoxide into reactive peroxy radicals, which initiate crosslinking of the functional polymer at ambient temperature. The stability of the latex composition prior to application onto a substrate can be demonstrated by measuring the KU viscosity of the formulation. As the following examples show, formulations shows excellent pot stability when the peroxidase enzyme and the hydrophobic hydroperoxide are phase separated. The examples further show the necessity of including both the peroxidase enzyme and the hydrophobic hydroperoxides to achieve enhanced post-cure performance.

The combination of peroxidase enzyme and stable hydrophobic hydroperoxide act as an efficient one-pot cure package with accelerated initial cure rate required for many practical application. The cure package has broader applicability in coatings formulated with waterborne (WB) latex binders bearing a variety of polymerizable functional groups.

EXAMPLES

Materials

Peroxidase enzyme was supplied as a liquid formulation (~10 mg/mL). Acrylic and alkyd master paints were prepared according to typical water based acrylic and alkyd paint formulations respectively. The cumene hydroperoxide was added to the paint and the peroxidase enzyme was added the following day.

Water Based Alkyd Paints Application Testings

The master alkyd paint formulation is shown in Table 1.

TABLE 1

Master Alkyd Paint Formulation

| Ingredients | Alkyd Master Paint (g) |
| --- | --- |
| Pigment Grind: | |
| Premix the next 4 ingredients: | |
| Water | 13.83 |
| Natrosol Plus 330 Rheology modifier | 0.12 |
| Bentone EW Rheology modifier | 0.17 |
| AMP-95 ™ Dispersant | 0.10 |
| Add the next 5 ingredients to grind pot: | |
| Disperbyk 190 Dispersant | 0.41 |
| TRITON ™ CF-10 Non-ionic surfactant | 0.12 |
| Water | 5.07 |
| Rhodoline 643 Defoamer | 0.09 |
| ACRYSOL ™ RM-8W Thickener | 0.50 |
| Ti-Pure R-706 TiO$_2$ slurry | 60.13 |
| Grind Sub-total | 80.55 |
| Let Down: | |
| Hexion EX-868 Alkyd dispersion | 119.69 |
| BYK-011 Defoamer | 0.22 |
| Add Grind to Letdown | |
| Paint Sub-total | 200.45 |

(AMP-95, TRITON, and ACRYSOL are all Trademarks of The Dow Chemical Company or Its Affiliates.)

Drawdowns of the paints (5 mil wet on aluminum panels) were prepared for König testing and print resistance testing. All drawdowns were stored in the controlled temperature room (CTR) until use, and returned to the CTR between uses for König testing. König testing was done using the Byk Mallinckrodt König Pendulum Hardness Tester. Prior to König testing, each drawdown was evaluated by touching with a gloved finger. If the drawdown was judged to be too tacky, the König value was not measured. Each König value was reported as the average of two measurements. Print resistance testing was done according to a modification of Resistance Test Method 614 in which each drawdown was covered with a piece of aida cloth and four #8 rubber stoppers. Weights were then placed on the stoppers and the panels were left at 60° C. for 1 h. Following removal of weights and stoppers, the panels were allowed to cool to room temperature prior to removal of the cloth. The extent of print resistance was rated according to the scales previously reported.

The drier packages are shown in Table 2.

TABLE 2

Drier package and viscosity adjustment for alkyd paint

| Alkyd Paint ID | Comp 1 | Comp 2 | Comp 3 | Ex. 1 |
| --- | --- | --- | --- | --- |
| Binder solids mass | 15.9 g | 15.9 g | 15.9 g | 15.9 g |
| Pre-paint Mass | 50 g | 50 g | 50 g | 50 g |
| Dryers: | None | DSM Peroxidase | DSM Peroxidase | DSM Peroxidase |
| Premix #1 | | | | |
| CHP (FR initiator) | — | — | — | 0.1 g |
| Water | 2 g | 2 g | 2 g | 2 g |
| Hydrogen Peroxide (30%) | — | — | 0.53 g | — |
| Premix #2 (Enzyme) | | | | |
| DSM peroxidase | — | 4.25 g | 4.25 g | 4.25 g |
| Water | 4.25 g | — | — | — |
| Adjust Final Viscosity to KU 100-105, ICI ~2.0: | | | | |
| ACRYSOL ™ RM-2020NPR Thickener | 2.36 g | 1.85 g | 2.35 g | 2.35 g |
| Total | 58.61 g | 58.10 g | 59.13 g | 58.70 g |

Water Based Alkyd Binders Cure Chemistry Testings

Infrared spectroscopy was used to investigate alkyd cure rate. The C—H stretch of allylic olefin has a distinct absorption at 3007 cm$^{-1}$. The progress of cure was monitored as a function disappearance of the C—H stretch. The plot of C—H stretch peak intensity as a function of time correlates with the kinetics of the initiation, propagation, and termination. Alkyd binder BF28-RC2 was chosen as a test system. The binder was formulated with various drier packages. The alkyd film was cast directly onto the diamond ATR with a 5-mil drawdown bar. Spectra were measured continuously with a custom OMNIC macro "cont2stginputdelay.mac." The unsaturated C—H stretch intensity at 3007 cm−1 was analyzed as a function of time. The control sample without any drier did not demonstrate significant cure after 300 h. The kinetic data of alkyd cure is presented in Table 4; $t_{1/2}$ refers to the time (h) for the film to reach half reaction.

TABLE 3

Application test results (König Hardness & Print resistence) for WB alkyd paints.

| WB Alkyd Paints | Comp. 1 | Comp 2 | Comp 3 | Ex. 1 |
| --- | --- | --- | --- | --- |
| König Hardness (s) | | | | |
| 1 d | 4 | 4 | 4 | 9 |
| 2 d | 6 | 7 | 6 | 12 |

TABLE 3-continued

Application test results (König Hardness & Print resistence) for WB alkyd paints.

| WB Alkyd Paints | Comp. 1 | Comp 2 | Comp 3 | Ex. 1 |
|---|---|---|---|---|
| 10 d | 7 | 10 | 9 | 14 |
| Print Resistance (Scale 1-10) | | | | |
| 2 d | 0 | 5 | 4 | 6.5 |
| 7 d | 1 | 7 | 6 | 8 |

TABLE 4

Kinetics of alkyd film cure in the presence of various driers

| Drier Package | Induction time (h) | Half life (h) after induction period | $t_{1/2}$ (h) |
|---|---|---|---|
| No drier | No cure (after 300 h) | — | — |
| Peroxidase | 45 | 15 | 60 |
| Peroxidase + HOOH | 47 | 18 | 65 |
| Peroxidase + CHP | 0 | 7 | 7 |

Water Based Acrylic Paints Application Testings

The master water based acrylic paint was prepared according to typical water based acetoacetoxy functionalized acrylic paint formulations following the formulation sheet as shown in Table 5. The drier package was added to the master paint and final KU and ICI were adjusted using ACRYSOL™ RM-2020NPR Thickener. Drawdowns of the paints (5 mil wet on aluminum panels) were prepared for König testing. All drawdowns were stored in the controlled temperature room (CTR) until use, and returned to the CTR between uses in the case of the König testing. König testing was done using the Byk Mallinckrodt König Pendulum Hardness Tester. Each König value is reported as the average of two measurements. Paint Formulations for Comparative Examples 4-6 and Example 2 are shown in Table 6 and application test results are shown in Table 7.

TABLE 5

Master acrylic paint formulation

| Ingredients | Acrylic Master Paint (g) |
|---|---|
| RHOPLEX ™ HG-95P Emulsion Polymer | 282.76 |
| BYK-024 Defoamer | 0.48 |
| Water | 19.22 |
| TAMOL ™ 2002 Dispersant | 0.96 |
| Ammonia (28%) | 0.12 |
| Ti-Pure R-746 $TiO_2$ slurry | 145.07 |
| Propylene Glycol | 7.21 |
| TRITON ™ X-100 octylphenol ethoxylate | 2.11 |
| BYK-024 Defoamer | 0.96 |
| KATHON ™ LX Microbiocide (1.5%) | 0.73 |
| ACRYSOL ™ RM-2020 NPR Thickener | 9.61 |
| Grind Sub-Total | 469.22 |
| Texanol coalescent | 15.78 |
| Water | 15.07 |
| Total | 500.07 |

(TAMOL, KATHON, AND ACRYSOL are Trademarks of The Dow Chemical Company or Its Affiliates.)

The composition for RHOPLEX™ HG-95P Emulsion Polymer is 40% (45% butyl acrylate/53.5% methyl methacrylate/0.5% methacrylic acid/1.0% allyl methacrylate)//60% (35% butyl acrylate/47.5% methyl methacrylate/2.5% methacrylic acid/15% acetoacetoxyethyl methacrylate).

TABLE 6

Drier package and Viscosity Adjustment for Acrylic Paint

| Acrylic Paint ID | Comp 4 | Comp 5 | Comp 6 | Ex 2 |
|---|---|---|---|---|
| Binder solids mass | 26.29 g | 26.29 g | 26.29 g | 26.29 g |
| Pre-paint Mass | 100 g | 100 g | 100 g | 100 g |
| Dryers: | None | DSM Peroxidase | DSM Peroxidase | DSM Peroxidase |
| Premix #1 | | | | |
| CHP (FR intiator) | — | — | — | 0.13 g |
| Hydrogen peroxide | — | — | 0.88 | — |
| Premix #2 (Enzyme) | | | | |
| DSM peroxidase | — | 7.3 g | 7.3 g | 7.3 g |
| Water | 7.3 g | — | — | — |
| Adjust Final Viscosity to KU 100-105, ICI ~2.0: | | | | |
| ACRYSOL™ RM-2020NPR | 2.12 g | 2.26 g | 2.20 g | 2.18 g |
| Actual Totals | 109.42 g | 109.56 g | 110.38 g | 109.61 g |

TABLE 7

Application Test Results (König Hardness) for Water-Based Acrylic Paints.

| WB Alkyd Paints | Comp 4 | Comp 5 | Comp 6 | Ex 2 |
|---|---|---|---|---|
| König Hardness (s) | | | | |
| 1 d | 14 | 11 | 10 | 24 |
| 2 d | 15 | 11 | 10 | 28 |
| 10 d | 21 | 15 | 14 | 36 |

Cure Chemistry of Waterborne Vinyl Functionalized Silicone Emulsion

The waterborne vinyl functionalized silicone emulsion was used as is. The cure performance of the silicone emulsion formulated with cumene hydroperoxide and peroxidase enzyme was studied as function of extractable unreacted macromer (by FTIR spectroscopy) trapped within cure film. The results are presented in Table 8.

TABLE 8

Vinyl Functionalized Aqueous Silicone Emulsion Cure Chemistry as Function of Extractable Percent and Tensile Strength

| Drier Package | Percent extractable | Tensile Strength |
|---|---|---|
| No drier | 25 | Not cured to measure |
| Peroxidase | 28 | Not cured to measure |
| Peroxidase + CHP | 1.6 | 4.7 MP |

In waterborne silicone emulsions, the cure performance is typically studied by extracting unreacted macromer trapped in the film. When both CHP and peroxidase are present in the formulation, the extractables from room temperature cured film is below 2%. The tensile strength of cured film using hydroperoxides-peroxidase drier package is comparable to those cured by peroxides at higher temperature.

Pot-life Stability Measurements

The pot life of alkyd and acrylic paints at room temperature and heat-age temperatures (45° C.) were monitored by KU viscosity measurements and were found to be stable for at least 6 weeks. No visible gelation was observed in any of the systems. Table 9 shows pot life stability for the alkyd and acrylic paint as well as the vinyl-functionalized silicone emulsion. $KU_o$ refers to the initial KU viscosity in Krebs units; $KU_{RT(f)}$ is the KU viscosity after six weeks at room temperature storage; $KU_{A(f)}$ is the KU heat aged viscosity (45° C.) after six weeks of heat aging.

TABLE 9

Pot Life Stabilities

| Drier Package | $KU_o$ | $KU_{RT(f)}$ | $KU_{A(f)}$ |
|---|---|---|---|
| Alkyd Paint (Ex 1) | 104.5 | 105.1 | 103.5 |
| Acrylic Paint (Ex 2) | 92 | 95 | 94 |
| Silicone emulsion (Ex 3) | 58 | 60 | 60 |

The invention claimed is:

1. A composition comprising a stable aqueous dispersion of crosslinkable polymer particles, a peroxidase enzyme, and a hydrophobic hydroperoxide having a 10-hour half life temperature of at least 100° C., wherein the dispersion of crosslinkable polymer particles is an alkyd based latex, an acetoacetoxy functionalized acrylic-based latex, a vinyl acetate based latex, or a vinyl siloxane based latex; wherein the concentration of the peroxidase enzyme is from 0.1 to 1.1 weight percent, based on the weight of the latex; the concentration of the hydrophobic hydroperoxide is from 0.02 to 1 weight percent based on the weight of the latex; and the EPI-Suite calculated logP of the hydrophobic hydroperoxide is from 0.75 to 4.

2. The composition of claim 1 wherein the dispersion of crosslinkable polymer particles is an alkyd based latex.

3. The composition of claim 1 wherein the dispersion of crosslinkable polymer particles is an acetoacetoxy functionalized acrylic-based latex.

4. The composition of claim 1 wherein the dispersion of crosslinkable polymer particles is a vinyl acetate based latex.

5. The composition of claim 1 wherein the dispersion of crosslinkable polymer particles is a vinylsiloxane based latex.

6. The composition of claim 1 wherein the hydrophobic hydroperoxide is cumene hydroperoxide, t-amyl hydroperoxide, t-butyl hydroperoxide, paramenthane hydroperoxide, isopropylcumyl hydroperoxide, or 1,1,3,3-tetramethybutyl hydroperoxide, or a combination thereof.

7. The composition of claim 6 wherein the hydrophobic hydroperoxide is cumene hydroperoxide.

8. A method comprising the steps of 1) contacting together a stable aqueous dispersion of crosslinkable polymer particles, a peroxidase enzyme, a hydrophobic hydroperoxide having a 10-hour half life temperature of at least 100° C., a pigment, and a rheology modifier; and 2) applying the mixture from step 1) to a substrate to form a cured coating; wherein the dispersion of crosslinkable polymer particles is an alkyd based latex, an acetoacetoxy functionalized acrylic-based latex, a vinyl acetate based latex, or a vinyl siloxane based latex; wherein the concentration of the peroxidase enzyme is from 0.1 to 1.1 weight percent, based on the weight of the latex; the concentration of the hydrophobic hydroperoxide is from 0.02 to 1 weight percent based on the weight of the latex; and the EPI-Suite calculated logP of the hydrophobic hydroperoxide is from 0.75 to 4.

9. The method of claim 8 wherein the crosslinked coating is cured at ambient temperature.

* * * * *